US007704495B2

(12) United States Patent
Yanaga

(10) Patent No.: US 7,704,495 B2
(45) Date of Patent: Apr. 27, 2010

(54) PROCESS FOR PRODUCING CARTILAGE CELLS FOR TRANSPLANTATION

(75) Inventor: Hiroko Yanaga, Ambient Kokura 912, 16-1, Kumamoto 3-chome, Kokurakita-ku, Kitakyusyu-shi, Fukuoka, 802-0044 (JP)

(73) Assignees: Hiroko Yanaga, Fukuoka (JP); Katsu Yanaga, Fukuoka (JP)

( * ) Notice: Subject to any disclaimer, the term of this patent is extended or adjusted under 35 U.S.C. 154(b) by 0 days.

(21) Appl. No.: 10/552,000

(22) PCT Filed: Apr. 8, 2004

(86) PCT No.: PCT/JP2004/005071

§ 371 (c)(1),
(2), (4) Date: Oct. 4, 2005

(87) PCT Pub. No.: WO2004/092359

PCT Pub. Date: Oct. 28, 2004

(65) Prior Publication Data

US 2006/0088506 A1    Apr. 27, 2006

(30) Foreign Application Priority Data

Apr. 15, 2003  (JP) .............................. 2003-109707
Jun. 20, 2003  (JP) .............................. 2003-176351

(51) Int. Cl.
*A01N 65/00* (2006.01)
(52) U.S. Cl. .................. 424/93.7; 424/423; 435/29; 435/373
(58) Field of Classification Search .............. 424/423, 424/93.7; 435/366, 378
See application file for complete search history.

(56) References Cited

U.S. PATENT DOCUMENTS

2001/0014473 A1    8/2001   Rieser et al.

FOREIGN PATENT DOCUMENTS

| EP | 1 331 264 A1 | 7/2003 |
| EP | 1331264 A1 * | 7/2003 |
| WO | WO-02/012451 A1 | 2/2002 |
| WO | WO-2004/092359 A1 | 10/2004 |

OTHER PUBLICATIONS

Merriam Webster online dictionary http://www.m-w.com/dictionary/perichondrium.*
Van osch et al , Chondrogenic Potential of in vitro multiplied rabbit perichondrium cells cultured in alginate beads in defined medium, Tissue Engineering,vol. 6 , 2000 p. 321-330.*
Yi et al, Journal of Korean Soc. Plast. Reconstru. Surg, vol. 28, 2001 Abstract.*
Suchesten et al , Variations in the appearance of human elastic cartilage, THe Ohio Journal of Science, vol. 6, 1969, p. 366-371.*
Megerian et al., Minimally invasive technique of auricular cartilage harvest for tissue engineering, Tissue Engineering, vol. 6, 2000, p. 69-74.*
Adachi, Nobuo et al., "Soshiki Kogaku ni Motozuku Baiyo Nankotsu Saibo Ishoku", Igaku no Ayumi, 2002, vol. 200, No. 3, pp. 258-259.
Brittberg M. et al., Treatment of deep cartilage defects in the knee with autologous chondrocyte transplantation, N. Engl. J. Med., 1994, vol. 331, No. 14, pp. 889-895.
Matsuda, Kazuya et al., "Jinko Nankotsu Sakusei no Kokoromi", Igaku no Ayumi, 1995, vol. 172, No. 6, pp. 390-391.
Brittberg et al., The New England Journal of Medicine, vol. 331, No. 14, pp. 889, 895, 1994.
Hyojun Seikeigekagaku, Standard Orthopaedics, Third Edition, with partial translation.
Bently et al., Nature, vol. 230, pp. 385-388, 1971.
Green, Clinical Orthopaedics and Related Research, vol. 124, pp. 237-250, 1977.
Wakitani et al., The Journal of Bone and Joint Surgery, vol. 71-B, No. 1, pp. 74-80, 1989.
Paige et al., Plastic and Reconstructive Surgery, vol. 96, No. 6, pp. 1390-1398, 1995.
Paige et al., Plastic and Reconstructive Surgery, vol. 97, No. 1, pp. 168-178, 1996.
Aulthouse et al., In Vitro Cellular & Developmental Biology, vol. 25, No. 7, pp. 659-668, 1989.
Ting et al. Annuals of Plastic Surgery, vol. 40, No. 4, pp. 413-421, 1998.
Rodriguez et al., Plastic and Reconstructive Surgery, vol. 103, No. 4, pp. 1111-1119, 1999.
Vacanti et al., Plastic and Reconstructive Surgery, vol. 88, No. 5, pp. 753-759, 1991.
Cao et al., Plastic and Reconstructive Surgery, vol. 100, No. 2, pp. 297-303, 1997.
Aston et al., The Journal of Bone and Joint Surgery, vol. 68-B, No. 1, pp. 29-35, 1986.
Nevo et al., Cell Biology International, vol. 17, No. 3, pp. 255-273, 1993.
Nixon et al., Am J Vet Res, vol. 54, No. 2, pp. 349-354, 1993.
Mok et al., The Journal of Biological Chemistry, vol. 269, No. 52, pp. 33021-33027, 1994.
Cohen et al., Biomaterials, vol. 21, pp. 2117-2123, 2000.
The 48th Annul Meeting of Japan Society of Plastic and Reconstructive Surgery, Apr. 13-15, 2005, with English translation.
Chesterman et al., J. Bone Joint Surg. Br., vol. 50, pp. 184-197 (1968).

(Continued)

*Primary Examiner*—Ralph Gitomer
*Assistant Examiner*—Tiffany M Gough
(74) *Attorney, Agent, or Firm*—Birch, Stewart, Kolasch & Birch, LLP

(57) ABSTRACT

This invention is intended to provide a method to quickly obtain a large amount of normal human chondrocytes or a mass thereof without fear of bacterial or viral infection. Namely, a method of producing human chondrocytes characterized by comprising co-culturing chondrocytes obtained from a cartilage having perichondrium, for example, auricular cartilage together with the perichondrium; and a method of producing human chondrocytes characterized by comprising monolayer or multilayer seeding the cultured cells once or more and culturing to give a chondrocyte mass.

5 Claims, 3 Drawing Sheets
(1 of 3 Drawing Sheet(s) Filed in Color)

OTHER PUBLICATIONS

Skoog et al., Scand. J. Plast. Reconstr. Surg. vol. 6, pp. 123-125 (1972).

Hvid et al., Acta. Orthop. Scand. vol. 52, pp. 91-93 (1981).

Hommiinga et al., J. Bone Joint Surg. Br. vol. 72, pp. 1003-1007 (1990).

Matsuda et al., Igaku no Ayumi (Progress of Medicine) vol. 172, No. 6, pp. 390-391 (1995).

Fujisato et al., Biomaterial, vol. 17, pp. 155-162 (1996).

van Osch et al., Igaku no Ayumi ( Progress of Medicine) vol. 107, pp. 433-440 (2001).

Brittberg et al., Clin. Orthrop. vol. 391, pp. 337-348 (2001).

Adachi et al., Igaku no Ayumi (Progress of Medicine) vol. 200, No. 3, pp. 258-259 (2002).

Edited by Fujii et al., "Biology of bones and cartilages: Development from basic medicine to clinical medicine" pp. 143-149 (Kinbara Syuppan K.K. 2002).

Ochi et al., J. Bone Joint Surg. Br. vol. 84-B, No. 4, pp. 571-578 (2002).

Yanaga et al., aesth. Plast. Surg. vol. 28, pp. 212-221 (2004).

Larson, et al., "Retention of the Native Chondrocyte Pericellular Matrix Results in Significantly Improved Matrix Production", Matrix Biology: Journal of the International Society for Matrix Biology, vol. 21, No. 4, pp. 349-359, Jun. 2002 (XP002378758).

Long, et al., "Regulation of Growth Region Cartilage Proliferation and Differentiation by Perichondrium", Development, vol. 125, No. 6, pp. 1067-1073, Mar. 1998 (XP002378759).

Di Nino, et al., "Regulation of Endochondral Cartilage Growth in the Developing Avian Limb: Cooperative Involvement of Perichondrium and Periosteum", Development Biology, vol. 240, No. 2, pp. 433-442, Dec. 15, 2001, (XP002378760).

Klein-Nulend, et al., "Stimulation of Cartilage Differentiation by Osteogenic Protein-1 in Cultures of Human Perichondrium", Tissue Engineering, vol. 4, No. 3, pp. 305-313, Oct. 1998, (XP009065726).

Nakamata, et al., "In Vitro Demonstration of Cell-to-Cell Interaction in Growth Plate Cartilage Using Chondrocytes Established From p53-/-Mice", Journal of Bone and Mineral Research: The Official Journal of the American Society for Bone and Mineral Research, vol. 18, No. 1, pp. 97-107, Jan. 2003, (XP 009065762).

Luan, et al., "Culture of Chondrocytes Using Allogenous Acellular Cartilaginous Matrix", Chinese Journal of Plastic Surgery and Burns, vol. 15, No. 3, pp. 178-179, May 1999 (XP002378761).

Zerega, et al., "Parathyroid Hormone [PTH(1-34)] and Parathyroid Hormone-Related Protein [PTHrP(1-34)] Promote Reversion of Hypertrophic Chondrocytes to a Prehypertrophic Proliferating Phenotype and Prevent Terminal Differentiation of Osteoblast-like Cells", Journal of Bone and Mineral Research Official Journal of the American Society for Bone and Mineral Research, vol. 14, No. 8, pp. 1281-1289, Aug. 1999 (XP002378762).

Vortkamp, "Interaction of Growth Factors Regulating Chondrocyte Differentiation in the Developing Embryo", vol. 9, Suppl A, pp. S109-S117, 2001 (XP009065754).

* cited by examiner

PROCESS FOR PRODUCING CARTILAGE CELLS FOR TRANSPLANTATION This application is a U.S. National Stage under 35 U.S.C §371 of International Application No. PCT/JP04/05071 (filed Apr. 8, 2004), which claims priority under 35 U.S.C. §119 (a)-(d) to Application No. JP2003-109707 filed on Apr. 15, 2003 and JP2003-176351 filed Jun. 20, 2003.

TECHNICAL FIELD

This invention relates to a method of producing normal human chondrocytes and the normal human chondrocytes obtained by the method. It also relates to a cartilage therapy material using the thus obtained normal human chondrocytes.

BACKGROUND ART

In a cartilage tissue, chondrocytes exist in the state of being embedded in the matrix. These chondrocytes can be separated from the matrix by treating the cartilage with an enzyme such as collagenase. Attempts have been made to utilize these separated chondrocytes in transplantation therapy, in particular, autotransplantation of chondrocytes for treating cartilage-related diseases. It has been experimentally confirmed that transplantation therapy with the use of this method is applicable to animals such as rabbits and cows from which a large amount of cells can be obtained (see, for example, Bentry, et al., Nature 230: 385-388 (1971), Green, Clin. Orthop. 124: 237-250 (1977); Wakitani et al., J. Bone and Joint Surgery 71B: 74-80 (1989); Paige et al., Plastic and Reconstructive Surgery 96:1390-1398 (1995); and Paige et al., Plastic and Reconstructive Surgery 97:168-178 (1996)).

Attempts have been also made to culture human chondrocytes in, for example, articular cartilage, auricular cartilage and costal cartilage (Aulthouse et al., In Vitro Cellular & Developmental Biology 25: 659-668 (1989); Brittberg et al., The New England Journal of Medicine 331: 889-895 (1994); Ting et al., Annals of Plastic Surgery 40: 413-421 (1998); and Rodriguez et al., Plastic and Reconstructive Surgery 103: 1111-1119 (1999)).

In humans, however, only a small amount of cartilage can be collected, therefore, only a small number of chondrocytes can be used at the initiation of the culture. Moreover, human chondrocytes can be minimally proliferated by the conventional methods and proliferated chondrocytes, if any are obtained, convert into fibroblasts having different characters. Thus, it is highly difficult to apply human chondrocytes to transplantation therapy in practice. Namely, there is a problem that although a large amount of normal chondrocytes is required for transplantation in humans, it has been impossible to obtain a sufficient amount of human chondrocytes using the currently available methods.

To overcome this problem, the present inventor proposed to quickly culture a large amount of human chondrocytes by co-culturing human chondrocytes together with perichondral cells in the chondrogenic stage serving as feeder cells supporting the proliferation ability of the chondrocytes (WO 02/12451 (2002)). The use of nonhuman animal feeder cells is, however, accompanied with problems of unexpected bacterial or viral infections and complicated treatments are needed to prevent these infections.

REFERENTIAL DOCUMENTS

1. Bentry, et al., Nature 230: 385-388 (1971)
2. Green, Clin. Orthop. 124:237-250 (1977)
3. Wakitani et al., J. Bone and Joint Surgery 71B: 74-80 (1989)
4. Paige et al., Plastic and Reconstructive Surgery 96:1390-1398 (1995)
5. Paige et al., Plastic and Reconstructive Surgery 97:168-178 (1996)
6. Aulthouse et al., In Vitro Cellular & Developmental Biology 25: 659-668 (1989)
7. Brrittberg et al., The New England Journal of Medicine 331: 889-895 (1994)
8. Ting et al., Annals of Plastic Surgery 40: 413-421 (1998)
9. Rodriguez et al., Plastic and Reconstructive Surgery 103: 1111-1119 (1999)
10. WO 02/12451 (2002)

DISCLOSURE OF THE INVENTION

An object of the present invention is to provide a method to quickly obtain a large amount of normal human chondrocytes or a mass thereof without fear of bacterial or viral infection. Another object of the present invention is to provide a cartilage therapy material with the use of the normal human chondrocytes or a mass thereof thus obtained. Accordingly, the present invention is as follows:

(1) A method of producing human chondrocytes characterized by comprising co-culturing chondrocytes obtained from a cartilage having perichondrium together with the perichondrium.

(2) The production method as described in the above (1) characterized in that the cartilage is auricular cartilage.

(3) The production method as described in the above (1) characterized by comprising monolayer or multilayer seeding of the cultured cells once or more and culturing to give a chondrocyte mass.

(4) The production method as described in the above (2) characterized by comprising monolayer or multilayer seeding the cultured cells once or more and culturing to give a chondrocyte mass.

(5) A cartilage therapy material comprising human chondrocytes obtained by a method as described in any of the above (1) to (4) either alone or together with an embedding material.

(6) The cartilage therapy material as described in the above (5) wherein the embedding material is one or more members selected from among collagen, polyglycolic acid, polylactic lacid, alginic acid, polyethylene oxide, fibrin adhesive, polylactic acid-polyglycolic acid copolymer, proteoglycan, glucosaminoglycan and human dermis.

BRIEF DESCRIPTION OF DRAWINGS

The patent or application file contains at least one drawing executed in color. Copies of this patent or patent application publication with color drawing(s) will be provided by the Office upon request and payment of the neccessary fee.

BEST MODE FOR CARRYING OUT THE INVENTION

Figure 1:
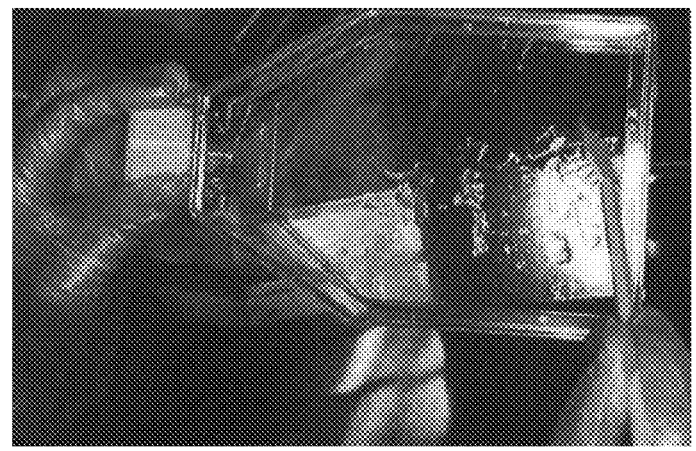
FIG. 1 presents a photograph showing a sheet-like gel mass obtained after multilayer culturing chondrocytes have been sub cultured for 2 weeks.

By further improving the preliminarily proposed method with the use of feeder cells (WO 02/12451 (2002)), the present inventor has established a more convenient method of culturing and proliferating chondrocytes such as auricular cartilage cells without resorting to feeder cells. Although it has been considered that feeder cells are required in culturing and proliferating chondrocytes, the present inventor has found out that chondrocytes can be cultured and proliferated without resorting to feeder cells. That is to say, the method according to the present invention can be conveniently carried out while omitting the troublesome procedures needed in the case of using feeder cells and, moreover, the risk of infection from the feeder cells and so on can be avoided thereby. Thus, it can be said that this method is highly safe and most suitable for autotransplantation in humans.

It has been further found out that a cartilage mass, which is obtained by multilayer culturing human chondrocytes that have been proliferated by the above-described method, is usable in transplantation therapy without resorting to a support.

In the case where the human cartilage to be used in the present invention is auricular cartilage, it is favorable from a cosmetic viewpoint to make a slight incision in the post auricular matrix skin and collect a cartilage tissue of a small size (about 1×1 cm$^2$). It is favorable that the thus collected cartilage tissue has perichondrium bonded to one face. Owing to this procedure, the cartilage can be quickly regenerated from the perichondrium remaining on the other face at the cartilage collection site and, as a result, the overall healing can be rapidly completed.

To obtain cells required for transplantation, the auricular cartilage having the perichondrium thus collected is finely diced and subjected to monolayer culture. In this step, it is preferable to employ a culture medium containing a cytokine required in the proliferation of the chondrocytes. Transplantation can be performed merely by using the cells obtained by this monolayer culture. By further subjecting the cells thus proliferated by the monolayer culture to multilayer culture several times, it is possible to obtain a tissue that has a high mechanical strength and therefore is durable when handled with instruments such as tweezers and never undergoes dispersion or absorption in vivo after transplantation. Although the number of multilayer seeding varies depending on the size of a desired tissue, it is generally preferable to carry out the multilayer seeding three or four times.

The thus obtained tissue is fed into an injection syringe or the like and, after attaching a needle, is then injected into a defect in a cartilage to thereby treat or repair nasal deformation, nose elevation, facial bone deformation, facial bone defect, gnathoplasty, skull deformation, skull defect, microtia or other diseases accompanied by a defect in a cartilage or a defective cartilage. In this step, the cartilage tissue may be used in the form of a mixture with a carrier selected from among collagen, polyglycolic acid (PGA), polylactic acid, alginate, polyethylene oxide, fibrin adhesive, polylactic acid-polyglycolic acid copolymer, proteoglycan or glucosaminoglycan. The chondrocytes obtained by the production method according to the present invention are practically usable as such without resorting to a carrier.

A. Human Chondrocytes

The method of producing chondrocytes according to the present invention can be applied to the culture of chondrocytes of any human cartilage tissue having perichondrium bonded thereto such as auricular cartilage, costal cartilage, intervertebral cartilage or tracheal cartilage. In particular, it is suitable for culturing and proliferating chondrocytes of auricular cartilage.

The chondrocytes to be used in the production method according to the present invention can be obtained from a human cartilage tissue having perichondrium by publicly known methods. It is generally preferable that an excised cartilage tissue is diced with a surgical knife or the like, treated with collagenase and then cultured and proliferated. For example, the process can be performed as follows.

1) A cartilage tissue is excised and disinfected by allowing to stand at about 4° C. overnight together with an antibiotic (for example, penicillin or kanamycin) or an antifungal agent (for example, amphotericin B). Then, the cartilage tissue is diced with a scalpel, etc.

2) The diced cartilage tissue is then transferred into a medium containing type II collagenase and allowed to stand at about 4° C. overnight. Next, it is shaken at 37° C. for 4 hours.

3) The thus treated tissue is centrifuged and the obtained precipitate (chondrocytes and perichondrium cells) is employed in the culture.

By this method, 3 to 5×10$^6$ chondrocytes can be obtained at the first generation of subculture from a human auricular cartilage tissue piece (1 cm$^2$). In the culture method according to the present invention, known growth factors can be used, especially ones capable of stimulating the proliferation of cartilage. Appropriately selected forms among FGF (for example, bFGF), IGF (for example, IGF-I), bone morphogenetic protein 9 (BMP-9) or combinations thereof.

B. Method of Culturing Human Chondrocytes

To culture human chondrocytes, use can be made of publicly known media suitable for culturing chondrocytes. In addition to fetal bovine serum (FBS) or human serum and hydrocortisone, the media may optionally contain a proliferation factor such as human bFGF or human IGF-I (Cuevas et. al., Biochem. Biophys. Res. Commun. 156, 611-618 (1988); and Froger-Gaillard et al., Endocrinol. 124, 2365-72). As an example of such a medium, DME(H) medium containing FBS (preferably about 10%), human bFGF (preferably about 10 ng/ml), hydrocortisone (preferably 40 ng/ml) and human IGF-I (preferably 5 ng/ml) can be cited. It is also possible to use autoserum obtained from a patient himself/herself so as to enhance the safety.

Next, the culture method according to the present invention will be described in greater detail.

1) Primary Culture

The chondrocytes are seeded in a medium contained in a flask and cultured in a CO$_2$ incubator under such conditions as being suitable for the culture of chondrocytes (for example, at 37° C. and 10% CO$_2$). The culture is continued until the proliferated cells form a confluent monolayer (usually for 10 to 14 days).

2) Subculture

The subculture can be carried out with the use of the same culture medium as the primary culture (usually 7 days per subculture). In the case of subculturing auricular cartilageorigin cells obtained by the primary culture, the cell count increases about 1000 times from P0 (primary culture) to P4. When a larger number of chondrocytes are needed, the subculture can be further repeated.

3) Multilayer Culture

A gel-like chondrocyte mass can be obtained by multilayer seeding and culturing the subcultured human chondrocytes once or more, preferably 3 to 4 times. In the chondrocyte mass thus obtained, the human chondrocytes are surrounded by a cartilage matrix containing aggrecan, etc. and the cells are bonded to each other via the matrix such as aggrecan to form a gel-like cell mass.

C. Cartilage Therapy Material

The above described sub cultured or multilayer cultured human chondrocytes or the cell mass obtained by the present invention, either as such or in the state of being embedded in a biomaterial, can be used in transplantation as a cartilage therapy material. Examples of the carrier in which the human chondrocytes or the cell mass can be embedded include collagen, polyglycolic acid (PGA), polylactic acid, alginate, polyethylene oxide, fibrin adhesive, polylactic acid-polyglycolic acid copolymer, proteoglycan, glycosaminoglycan and mixtures thereof.

By appropriately selecting and combining the carriers in which the chondrocytes are embedded, the cartilage therapy material can induce not only chondrogenesis but also cartilaginous ossification. As an example of the carrier enabling the induction of the cartilaginous ossification, human dermis may be cited. Moreover, it is possible to further promote the ossification by using a growth factor capable of promoting osteogenesis such as a bone morphogenetic protein (BMP).

To further illustrate the present invention in greater detail, and not by way of restriction, the following examples will be given.

EXAMPLE 1

Chondrocyte culture

Composition of culture medium: To the DME(H) medium, 10% of FBS, 10 ng/ml of human FGF (Kaken Pharmaceutical Research Institute), 40 ng/ml hydrocortisone (Sigma) and 5 ng/ml human IGF-I (GIBCO) were added.

Collected cartilage: From human rear auricular cartilage, a sample piece (about $1\times1$ cm$^2$) having perichondrium bonded to one face was collected.

(a) Chondrocyte Fraction

The cartilage piece obtained above was disinfected with penicillin G (800 u/ml), kanamycin (1 mg/ml) and Fungizone (2.5 ug/ml). It was then diced with a scalpel and then allowed to stand in F-12 medium containing 0.3% of type II collagenase (Worthington Biochemical) at 4° C. overnight. On the next day, the culture medium was shaken at 37° C. for 4 hours and centrifuged. The precipitate thus obtained was employed as a cell fraction at the initiation of the culture.

(b) Primary Culture

The cell fraction as described above was seeded by using the above-described medium in a flask having a base area of 75 cm$^2$. The cell fraction in this flask was cultured in a C)$_2$ incubator at a CO$_2$ concentration adjusted to 10%. The culture medium was replaced twice a week. As a result, the chondrocytes formed a confluent monolayer within a culture time of 10 to 14 days. The obtained cells were used for the following subculture.

It was confirmed that similar results were obtained by using, as the substitute for FBS, autoserum obtained by centrifuging the autoserum of a patient at 3000 rpm for 10 minutes.

(c) Subculture

Subculture was carried out by seeding $1\times10^6$ of the primary-cultured cells in a flask having a base area of 175 cm$^2$ and employing the same conditions as the primary culture. After culturing for 7 days, the cells formed a confluent monolayer. The obtained cells were employed in the next subculture. As a result, the cell count on the fourth subculture increased about 1000 times, compared with the cell count at the initiation of the subculture.

(d) Multilayer Culturing

Figure 2:
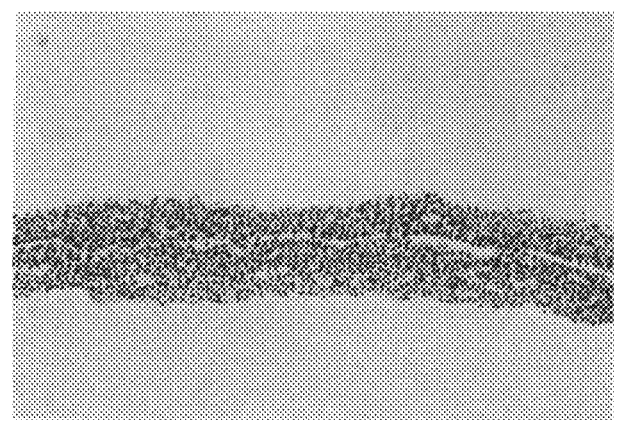
FIG. 2 presents a photograph showing the result of hematoxyl in-eosine staining of the gel-like chondrocyte mass shown in FIG. 1.
Figure 3:
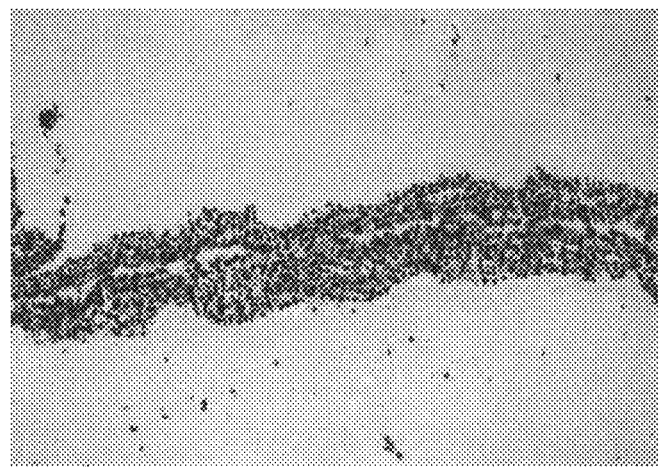
FIG. 3 presents a photograph showing the result of immunological staining for type II collagen serving as a cartilage tissue molecular marker.

The chondrocytes obtained by the subculture were seeded by overlaying thrice at a density of $1\times10^6$cells/cm$^2$ and cultured by multilayer culturing. After culturing for 2 weeks, a sheet-like gel mass was formed (FIG. 1). When the gel-like chondrocyte mass was stained with hematoxylin-eosine (HE), it was observed that the cells were multilayered and bonded together via the matrix (FIG. 2). When the cells were immunologically stained for type II collagen serving as a molecular marker of cartilage tissue, the extracellular matrix was stained, thus indicating that the extracellular matrix was a cartilage-specific matrix (FIG. 3).

EXAMPLE 2

Transplantation of Chondrocytes

Figure 4:
FIG. 4 presents a photograph showing the result of hematoxylin-eosine (HE) staining of a specimen sampled from a transplantation site.
Figure 5:
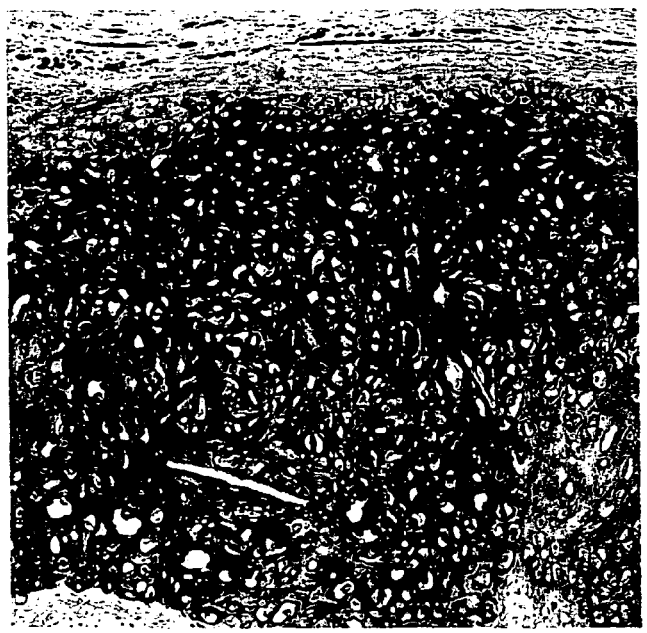
FIG. 5 presents a photograph showing the result of immunological staining of a specimen sampled from a transplantation site for type II collagen serving as a cartilage tissue molecular marker.
Figure 6:
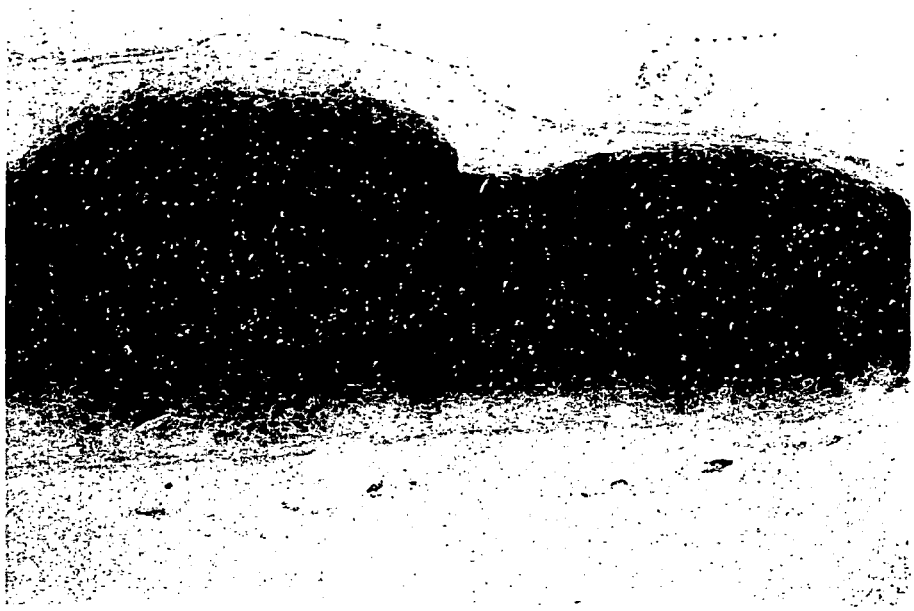
FIG. 6 presents a photograph showing the result of toluidine blue staining of a specimen sampled from a transplantation site.

First, the medium was removed from the culture flask and the cells were harvested with a cell lifter. Then the harvested cells were collected with a syringe. Next, the chondrocytes collected into the syringe were injected into a defect in a cartilage of a nude mouse by using an injection needle. Six months after the transplantation, a specimen was sampled from the transplantation site and histologically examined to confirm the success in engraftment. When the sampled tissue was stained with hematoxylin-eosine (HE), namely, it was observed that cells were multilayered and bonded to each other via the matrix (FIG. 4). When the cells were immunologically stained for type II collagen serving as a molecular marker of cartilage tissue, the extracellular matrix was stained, indicating that the extracellular matrix was a cartilage-specific matrix (FIG. 5). Moreover, metachromacia was shown in toluidine blue staining, indicating the presence of aggrecan serving as a cartilage marker (FIG. 6). These results indicated that the transplanted chondrocytes had formed a cartilage tissue.

INDUSTRIAL APPLICABILITY

According to the present invention, a large amount of normal human chondrocytes or a mass thereof can be quickly obtained in a large amount without fear of bacterial or viral infection.

The invention claimed is:

1. A method of proliferating human chondrocytes comprising:
1) collecting human cartilage having perichondrium;
2) treating the cartilage having perichondrium with type II collagenase;
3) centrifuging the treated cartilage having perichondrium in step 2) to obtain precipitate; and
4) culturing the precipitate of step 3),
wherein the chondrocytes and perichondrium are both in the culture, and wherein no non-human animal feeder cells are present in step 4), and further wherein the cells increase to $1\times10^6$ to $5\times10^6$ cells from 1 cm$^2$ tissue in primary culture and further increase at least 1000 times in subculture.

2. The method according to claim 1, wherein the cartilage is auricular cartilage.

3. The method according to claim 1, further comprising:
seeding the cultured chondrocytes in a monolayer or multilayer at least once; and culturing the chondrocytes until a chondrocyte mass forms.

4. The method according to claim 2, further comprising:
seeding the cultured chondrocytes in a monolayer or multilayer at least once; and culturing the chondrocytes until a chondrocyte mass forms.

5. The method according to claim 1, wherein the cells increase to $3\times10^6$ to $5\times10^6$ cells from 1 cm$^2$ tissue in primary culture.

* * * * *